US012176127B2

(12) United States Patent
Bertolote

(10) Patent No.: US 12,176,127 B2
(45) Date of Patent: Dec. 24, 2024

(54) FEEDTHROUGH FOR A MEDICAL DEVICE

(71) Applicant: Wyss Center for Bio and Neuro Engineering, Geneva (CH)

(72) Inventor: Tiago Bertolote, Le Grand-Saconnex (CH)

(73) Assignee: WYSS CENTER FOR BIO AND NEURO ENGINEERING, Geneva (CH)

( * ) Notice: Subject to any disclaimer, the term of this patent is extended or adjusted under 35 U.S.C. 154(b) by 0 days.

(21) Appl. No.: 18/708,795

(22) PCT Filed: Dec. 8, 2023

(86) PCT No.: PCT/IB2023/062422
§ 371 (c)(1),
(2) Date: May 9, 2024

(87) PCT Pub. No.: WO2024/127197
PCT Pub. Date: Jun. 20, 2024

(65) Prior Publication Data
US 2024/0331895 A1 Oct. 3, 2024

Related U.S. Application Data

(60) Provisional application No. 63/431,931, filed on Dec. 12, 2022.

(51) Int. Cl.
*H01B 17/26* (2006.01)
*A61N 1/375* (2006.01)

(52) U.S. Cl.
CPC ............ *H01B 17/26* (2013.01); *A61N 1/3754* (2013.01)

(58) Field of Classification Search
CPC .. H02G 3/22; H02G 3/24; H02G 3/26; H02G 3/30; H02G 3/34; H02G 15/025; F16L 5/10; F16L 5/00; F16L 5/02; H01B 17/26; H01B 17/00; H01B 17/005; H01B 17/265; A61N 1/375; A61N 1/3754; A61N 1/3756; A61N 1/3758; H01F 27/00; H01F 27/02
(Continued)

(56) References Cited

U.S. PATENT DOCUMENTS 8,013,433 B2    9/2011  Dalton et al.
8,288,654 B2 *  10/2012 Taylor ..................... A61N 1/05
                                                    174/152 GM
(Continued)

OTHER PUBLICATIONS

International Search Report and Written Opinion for Int'l Application No. PCT/IB2023/062422, entitled "Feedthrough for a Medical Device," consisting of 11 pages. Date Mailed: Feb. 27, 2024.

*Primary Examiner* — Angel R Estrada
(74) *Attorney, Agent, or Firm* — Hamilton, Brook, Smith & Reynolds, P.C.

(57) ABSTRACT

The present disclosure can provide an implantable feedthrough device including a feedthrough member formed of insulating material having opposing first and second surfaces. A series of conductors can extend through the feedthrough member between the first and second surfaces. The series of conductors can be arranged in a pattern that has an inner portion vacant of conductors for facilitating access for bonding wires to the conductors on at least one of the first and second surfaces of the feedthrough member.

23 Claims, 9 Drawing Sheets

(58) Field of Classification Search
USPC ... 174/650, 520, 652, 656, 260, 262, 138 R, 174/77 R, 152 GM; 361/302, 306.1, 600, 361/601; 333/182; 16/2.1, 2.2
See application file for complete search history.

(56) References Cited

U.S. PATENT DOCUMENTS

| | | | | |
|---|---|---|---|---|
| 8,536,468 | B2* | 9/2013 | Teske | A61N 1/3754 |
| | | | | 174/650 |
| 8,604,341 | B2* | 12/2013 | Barry | A61N 1/05 |
| | | | | 174/50.56 |
| 8,642,887 | B1* | 2/2014 | Li | A61N 1/3754 |
| | | | | 174/650 |
| 8,648,255 | B2* | 2/2014 | Talamine | A61N 1/3754 |
| | | | | 174/650 |
| 8,648,265 | B2* | 2/2014 | Talamine | A61N 1/3754 |
| | | | | 174/650 |
| 8,862,235 | B1 | 10/2014 | Stover et al. | |
| 9,008,779 | B2 | 4/2015 | Morioka et al. | |
| 11,298,555 | B2 | 4/2022 | Bhowmik | |
| 2005/0283203 | A1 | 12/2005 | Flaherty et al. | |
| 2006/0173259 | A1 | 8/2006 | Flaherty et al. | |
| 2017/0290521 | A1 | 10/2017 | Angle et al. | |
| 2019/0246929 | A1 | 8/2019 | Angle et al. | |
| 2021/0013051 | A1 | 1/2021 | Tolosa et al. | |
| 2022/0105349 | A1 | 4/2022 | Tompkins et al. | |

\* cited by examiner

FEEDTHROUGH FOR A MEDICAL DEVICE

RELATED APPLICATION

This application is the U.S. National Stage of International Application No. PCT/IB2023/062422, filed Dec. 8, 2023, which designates the U.S., and claims the benefit of U.S. Application No. 63/431,931, filed on Dec. 12, 2022, the entire teachings of which are incorporated herein by reference.

BACKGROUND

Implantable hermetic feedthrough devices can provide electrical connection between a bundle of wires connected to medical equipment and an implantable active medical device or implant, which can include implantable sensors and actuators. The present disclosure provides a feedthrough device that has a design that can allow a large number of wires to be easily bonded to the feedthrough device in a small area while maintaining the hermeticity of the implant, and can be suitable for automated bonding processes.

SUMMARY

The present disclosure can provide an implantable feedthrough device including a feedthrough member formed of insulating material having opposing first and second surfaces. A series of conductors can extend through the feedthrough member between the first and second surfaces. The series of conductors can be arranged in a pattern that has an inner portion vacant of conductors for facilitating access for bonding wires to the conductors on at least one of the first and second surfaces of the feedthrough member.

In particular embodiments, the series of conductors can be electrically connected to a respective series of pads that are arranged in a generally U-shaped pattern. The series of conductors can be electrically connected to the series of pads on the first and second surfaces of the feedthrough member. A portion of the pads can have a first geometric shape, and another portion of the pads can have a second geometric shape, for designating at least one of function, alignment and orientation. The pads having the first geometric shape can be circular in shape. In addition, the pads having the second geometric shape can be triangular shaped, with triangular points generally aligned in the direction of legs of the generally U-shaped pattern. The generally U-shaped pattern can have a generally round periphery, and a central slot separating the legs of the generally U-shaped pattern. The triangular shaped pads can be positioned at outer edges of the legs of the generally U-shaped pattern. The generally U-shaped pattern can be on a hexagonal grid centered on X and Y axes, with the central slot being centered along the Y axis. The pads that are circular in shape can be aligned in rows and columns along X and Y axis directions with consistent spacing, and the triangular points of the triangle shaped pads can be aligned in the direction of the Y axis, thereby facilitating automated alignment and orientation of the generally U-shaped pattern, and automated bonding of the wires to the conductors. An outer flange can be secured to the feedthrough member for supporting the feedthrough member. The series of conductors can include a greater number of conductors than is normally required for most applications, thereby providing additional auxiliary conductors. The pads having the circular shape can have a diameter of about 0.26 mm, a center to center spacing of about 0.38 mm, and can be 71 in number, whereby 64 pads and associated conductors are normally required for most applications. This can result in the additional auxiliary pads and associated conductors. The triangular shaped pads can have a base of about 0.34 mm and a height of about 0.73 mm.

The present disclosure can also provide a feedthrough device including a feedthrough member formed of insulating material having opposing first and second surfaces. A series of conductors can extend through the feedthrough member between the first and second surfaces. The series of conductors can be arranged in a generally U-shaped pattern having a generally round periphery and a central slot for facilitating access for bonding wires to the conductors on at least one of the first and second surfaces of the feedthrough member. The series of conductors can be electrically connected the pads on the first and second surfaces of the feedthrough member. A portion of the pads can have a circular shape, and two of the pads on opposite sides of the generally U-shaped pattern can have a triangular shape, for designating at least one of function, alignment and orientation.

The present disclosure can also provide a method of electrically connecting wires to a feedthrough device including providing a feedthrough member formed of insulating material having opposing first and second surfaces. A series of conductors can extend through the feedthrough member between the first and second surfaces. The series of conductors can be arranged in a pattern that has an inner portion vacant of conductors. The wires can be bonded to the conductors on at least one of the first and second surfaces of the feedthrough member. The pattern having the inner portion vacant of conductors can facilitate access for bonding the wires to the conductors.

In particular embodiments, the series of conductors can be electrically connected to a respective series of pads that are arranged in a generally U-shaped pattern. The series of conductors can be electrically connected to the series of pads on the first and second surfaces of the feedthrough member. A portion of the pads can have a first geometric shape, and another portion of the pads can have a second geometric shape, for designating at least one of function, alignment and orientation. The pads having the first geometric shape can be circular in shape. In addition, the pads having the second geometric shape can be triangular shaped, with triangular points generally aligned in the direction of legs of the generally U-shaped pattern. The generally U-shaped pattern can have a generally round periphery and a central slot separating the legs of the generally U-shaped pattern. The triangular shaped pads can be positioned at outer edges of the legs of the generally U-shaped pattern. The generally U-shaped pattern can be on a hexagonal grid centered on X and Y axes, with the central slot being centered along the Y axis. The pads that are circular in shape can be aligned in rows and columns along X and Y axis directions with consistent spacing. The triangular points of the triangular shaped pads can be aligned in the direction of the Y axis. Automated alignment and orientation of the generally U-shaped pattern and automated bonding of the wires to the conductors can be conducted. An outer flange can be secured to the feedthrough member for supporting the feedthrough member. Additional auxiliary conductors can be provided by including a greater number of conductors in a series of conductors than is normally required for most applications. The pads having the circular shape can have a diameter of about 0.26 mm, a center to center spacing of about 0.38 mm, and can be 71 in number, whereby 64 pads and associated conductors are normally required for most applications. This can result in additional auxiliary pads and associated conductors. The triangular shaped pads can have a base of about 0.34 mm and a height of about 0.73 mm.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

Figure 1:
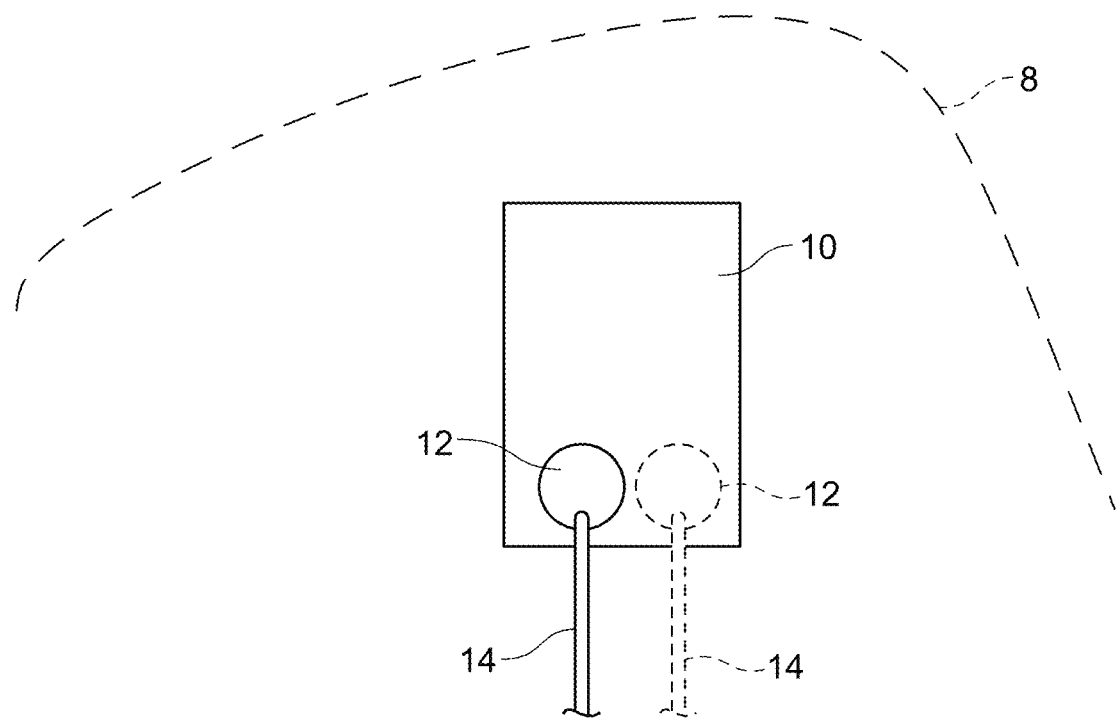
FIG. 1 is a schematic drawing of an implantable medical device or implant, implanted into a patient.

Referring to FIG. 1, an implantable medical device or implant 10 can be implanted into a patient 8, for example in the head, or other desired locations. The medical implant 10 can be electrically connected to an electrical feedthrough device 12 that is electrically connected to a bundle or cable 14 of electrical wires. The cable 14 can be electrically connected to a desired medical device or piece of equipment 11. In some embodiments, the cable 14 can connect to implantable sensors or actuators. Electrical signals and/or power can be conveyed to and/or from the medical implant 10 and device 11 (FIG. 2), through the cable 14 and the feedthrough device 12. Some embodiments of medical implant 10 can include more than one feedthrough device 12 connected thereto.

Figure 2:
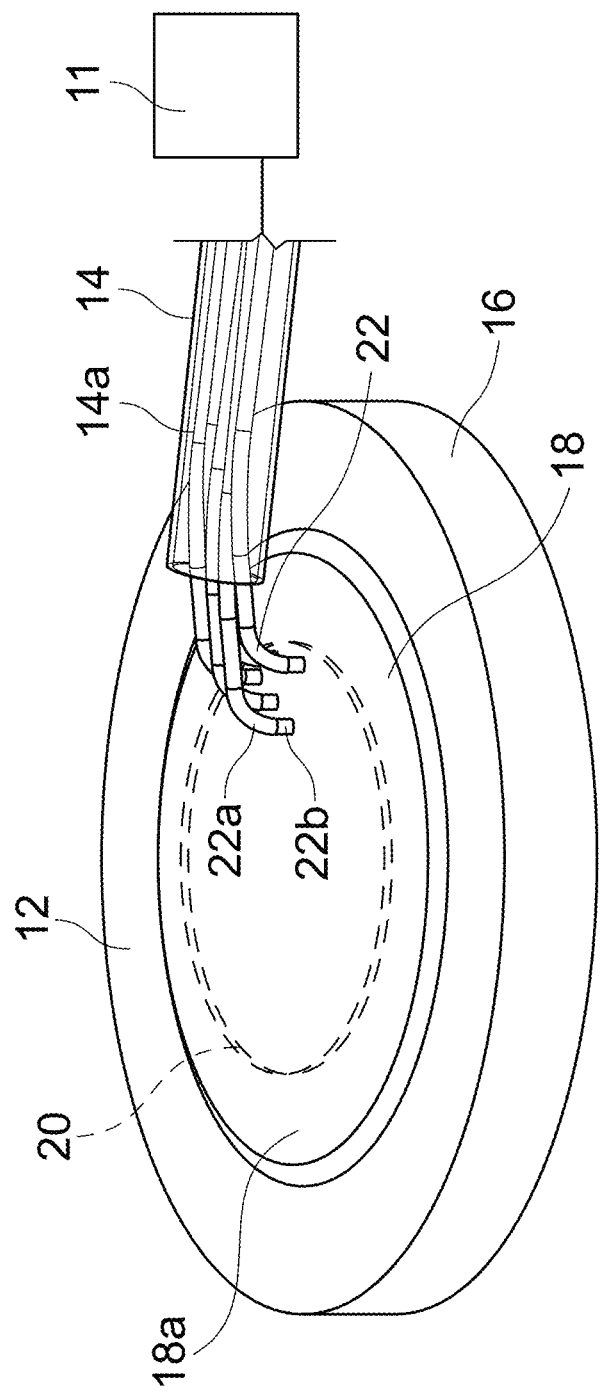
FIG. 2 is a perspective view of an embodiment of a feedthrough device in the present disclosure attached to a bundle of wires from a device.
Figure 3:
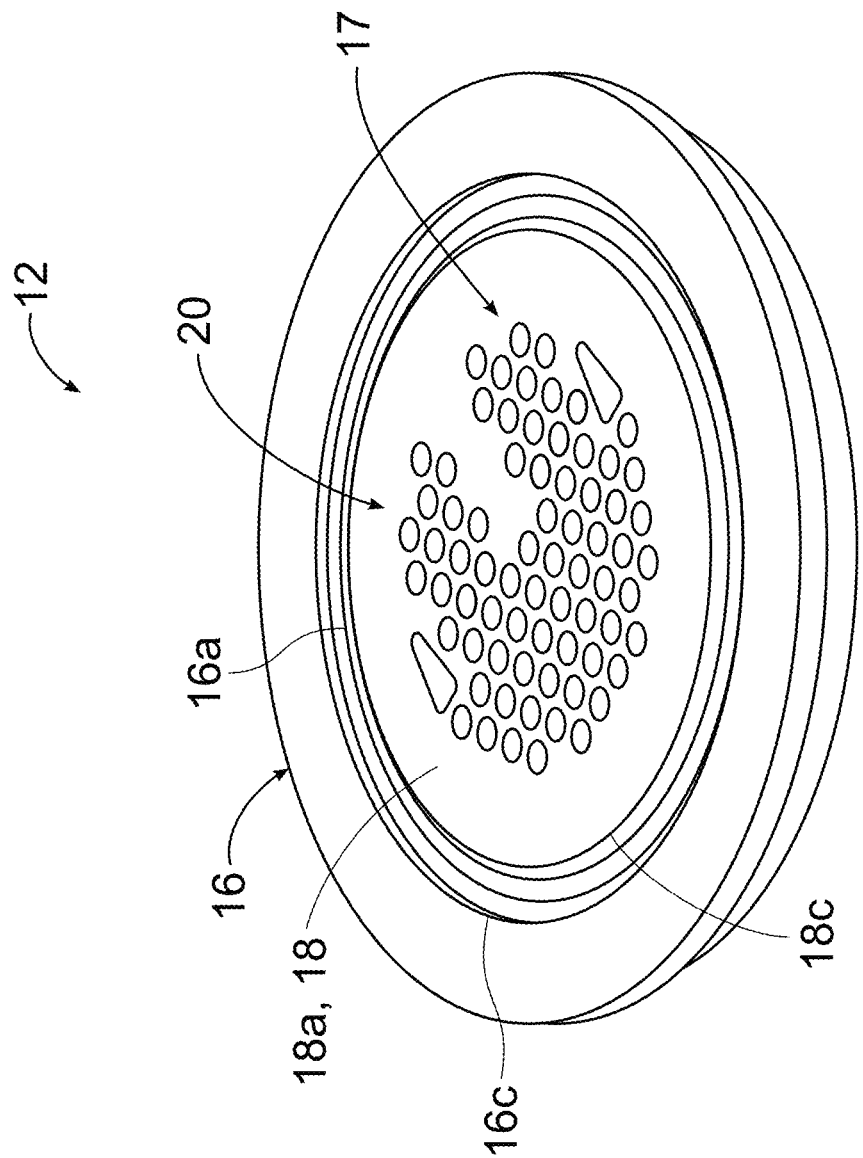
FIG. 3 is a perspective view of an embodiment of a feedthrough device in the present disclosure.
Figure 5:
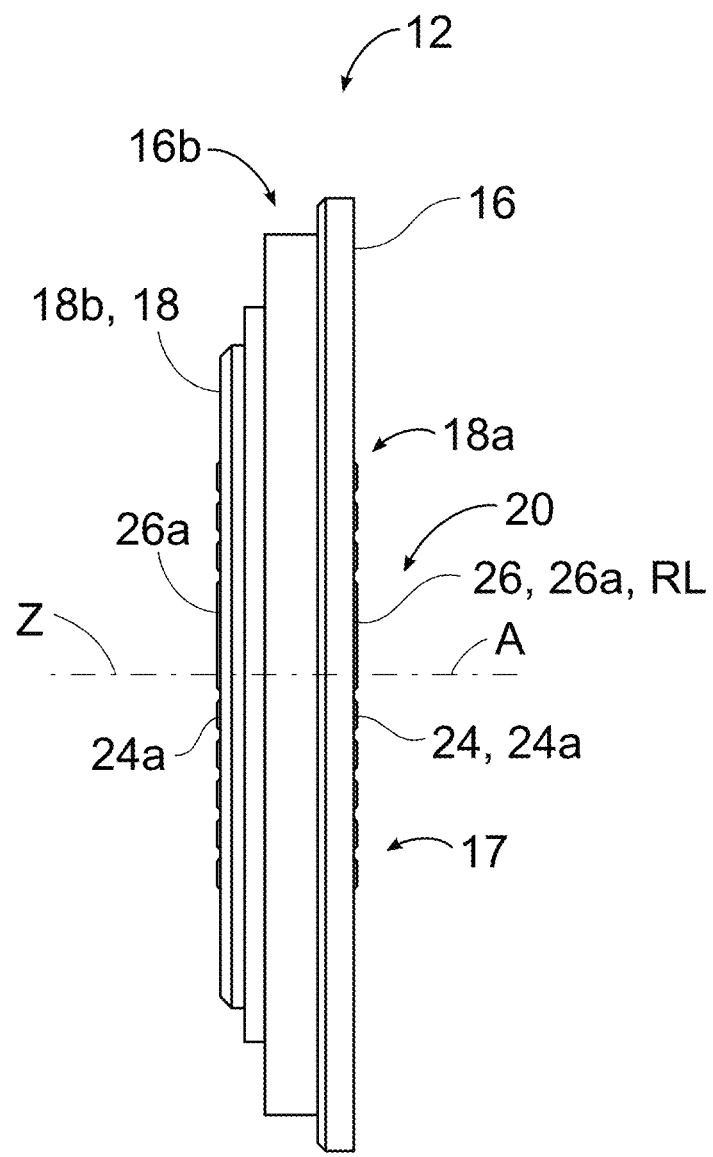
Figure 6:
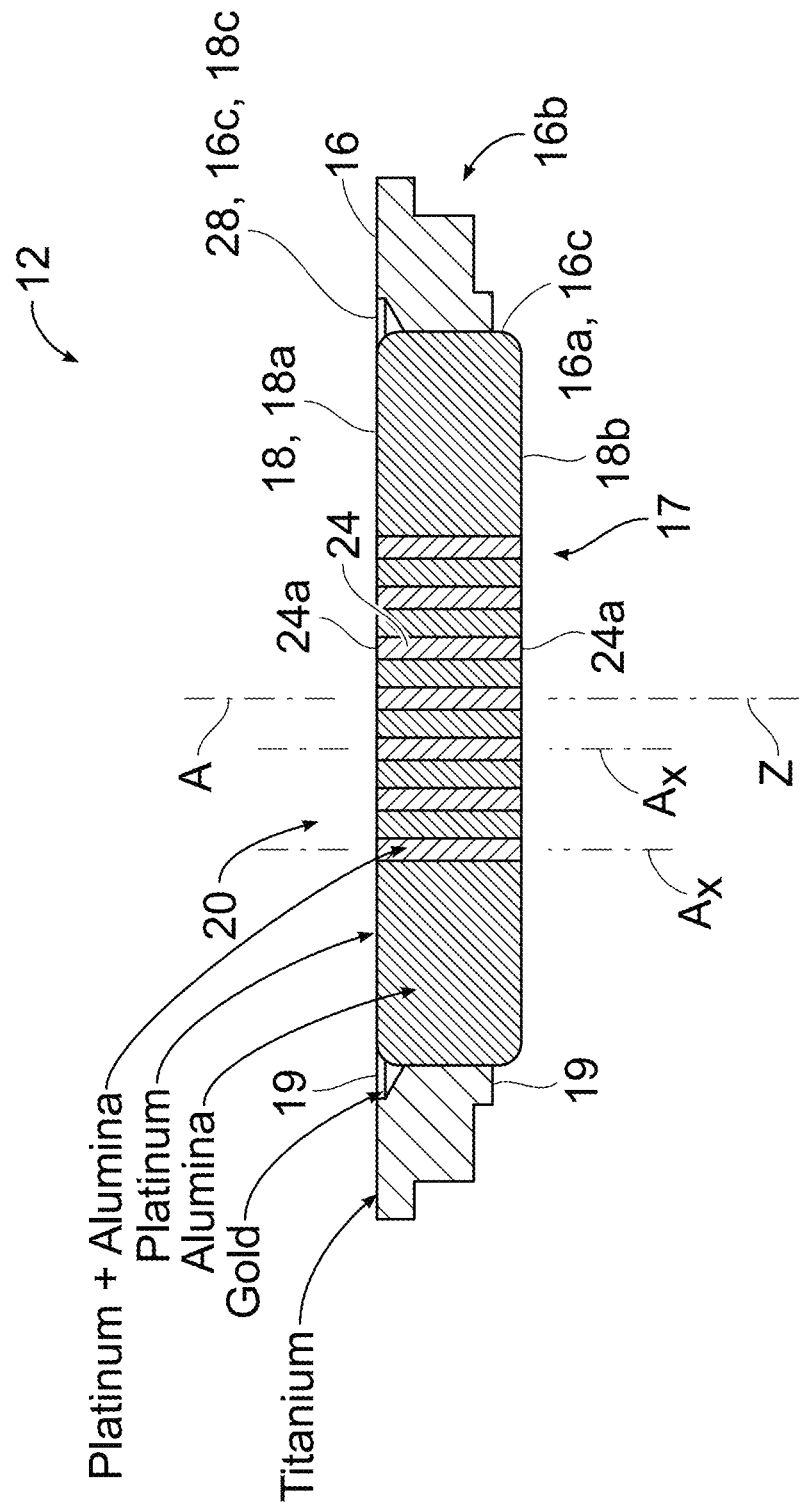

Referring to FIGS. 2 and 3, the feedthrough device 12 can include a round inner feedthrough disk or member 18 that is secured or supported within a round or annular outer flange 16. The feedthrough member 18 can include an insulative body with a pattern or series of electrical conductors 17 extending therethrough insulated from each other, from a first or top surface, side or face 18a, to a second or bottom surface, side or face 18b, in the direction of central axis A (FIGS. 4 and 5) which is in the Z axis direction, each along respective axes A and $A_x$ (FIG. 6). The pattern of conductors 17 can be in a generally U-shaped pattern 20. The cable 14 can include or contain a number or plurality of individual wires 22 within a sheath 14a. Each wire 22 can have a layer of insulation 22a, and an exposed electrically conductive metal tip 22b that can be bonded to selected respective electrically conductive electrical connection pads 24a and 26a of conductors 24 and 26, by a bonding apparatus 4. Bonding can be by suitable methods, including welding, brazing, soldering, adhesives, etc.

Figure 8:
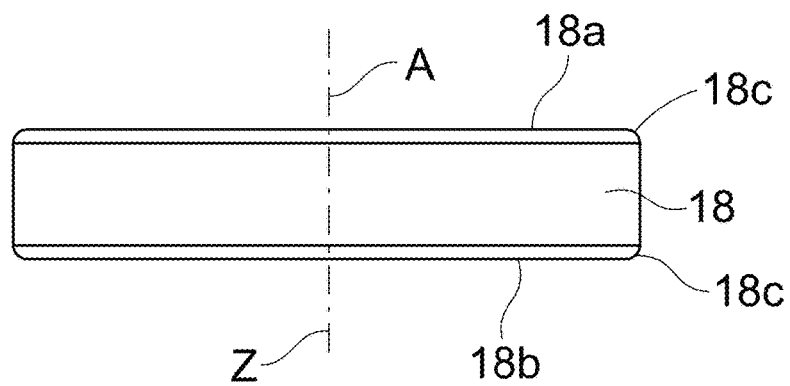

Referring to FIGS. 3-6, the outer flange 16 can have a round central hole or opening 16a (FIGS. 12 and 13) in which the feedthrough member 18 is secured or bonded, for example, by brazing with braze material 28 such as gold. The outer flange 16 can be metal or metallic, for example titanium metal, and can have outer circular shoulders 16b for mounting to the medical implant 10 and properly positioning the pads 24a and 26a on the bottom surface 18b of the feedthrough member 18 relative to the medical implant 10. The feedthrough member 18 can have an insulative ceramic disk that can be made of alumina. The hole 16a in the outer flange 16 can have chamfers 16c at opposite ends of the hole 16a (FIG. 13), and feedthrough member 18 can have chamfers 18c on the outer diameter (FIG. 8). When the feedthrough member 18 and outer flange 16 are assembled together, the chamfers 18c and 16c can provide two annular grooves 19 between the outer flange 16 and the feedthrough member 18 on opposite sides of outer flange 16, in which the braze material 28 or gold can fill or occupy and provide a strong hermetically sealed bond therebetween. In some embodiments, the outer diameter or width of the outer flange 16 and the feedthrough device 12 can be about 7.9 mm (0.31 inches).

Referring to FIGS. 4-9, the feedthrough member 18 can be generally puck or disk-shaped and formed of alumina, that can be $Al_2O_3 > 99.7\%$. The pattern or series of conductors 17 can include a first set, group, portion or series, of multiple, a number of, or plurality of conductors 24 and respective pads 24a, and a second set, group, portion or series of two conductors 26 and respective pads 26a on opposite right and left sides. The conductors 24 and 26 can pass through the feedthrough member 18 from the top surface 18a to the opposite or bottom surface 18b, to provide multiple, a number of, or a plurality of separate electrical paths, channels, wires or vias through the feedthrough member 18 between surfaces 18a and 18b that can be insulated from each other. Each conductor 24 can be electrically connected to or include, and aligned with, a curved, round or circular pad 24a on the top 18a and bottom 18b surfaces, and each conductor 26 can be electrically connected to or include, and aligned with, a triangle or triangular shaped pad 26a on the top 18a and bottom 18b surfaces. In some embodiments, the pads 24a can be elliptical in shape. The conductors 24 and 26 can be formed of platinum and alumina ($PT > 99.9\% + Al_2O_3 > 99.7\%$), and the pads 24a and 26b can be formed of metal such as platinum ($PT > 99.9\%$). Embodiments of conductors 26 can be similar to conductors 24 as shown, or can be larger in size.

The pattern of conductors 17 can be arranged in a generally U-shaped configuration, arrangement or pattern 20 that can be centered about central axis A along the Z axis, and also along the central X and Y (horizontal and vertical) axes in an XY grid. The XY grid can be in a hexagonal shaped pattern or hexagonal grid, which can be more compact than a square grid. The U-shaped pattern 20 of the conductors 24 and 26 can also result in a U-shaped pattern 20 of the pads 24a and 26a. The U-shaped pattern 20 can have a thick shape with a generally round or hexagonal perimeter or periphery 20a, and an inwardly extending central, center or middle gap or slot 20b of space that is vacant of or without conductors or pads. The slot 20b can be centered and extend along the central Y axis, and separate upwardly directed legs 20c of the U-shaped pattern 20. The thickened generally U-shaped pattern 20 of conductors 17 can have a shape where the bottom half has a generally full semicircular shape, and the top half has a slotted semicircular shape.

Figure 4:
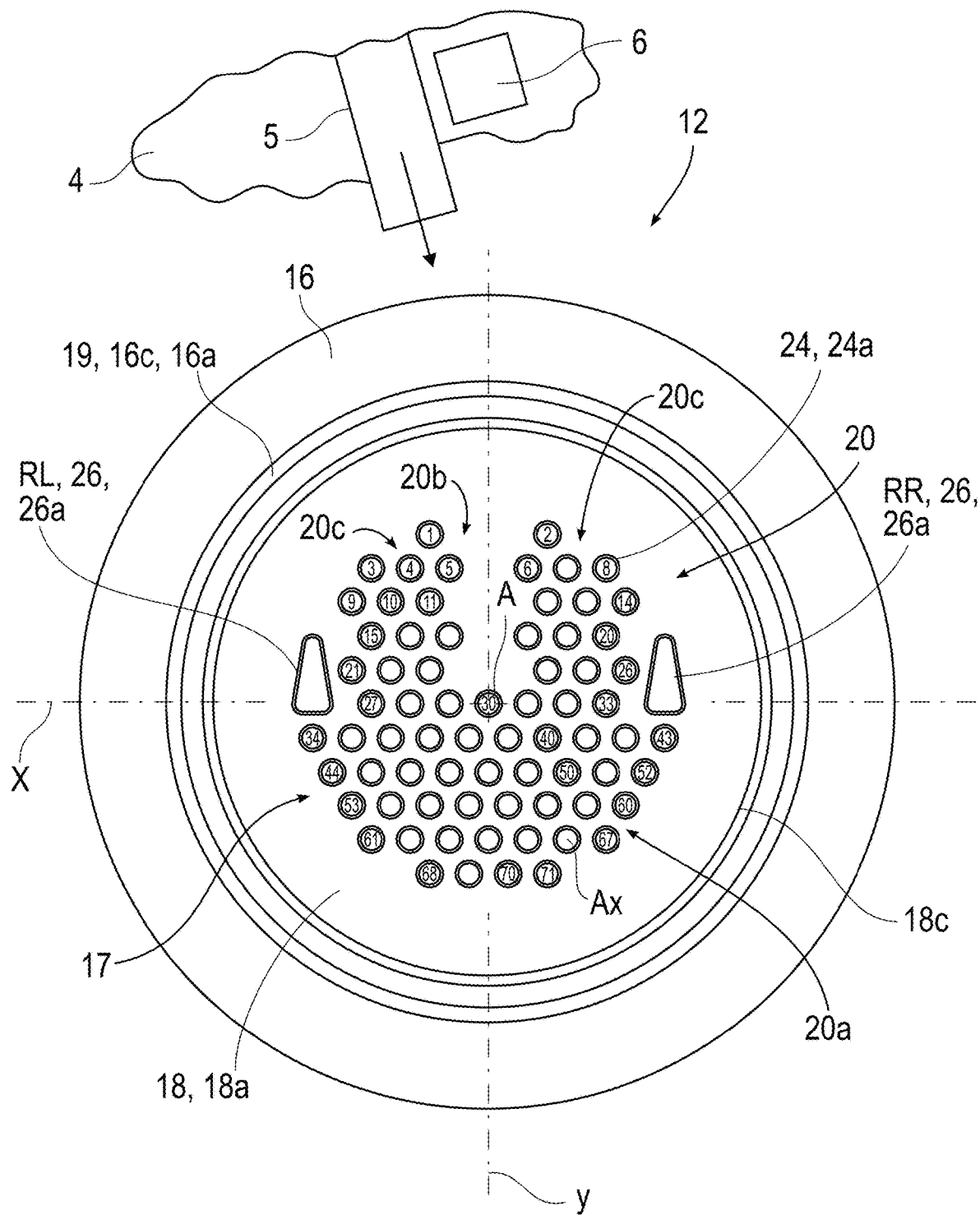
FIGS. 4-6 are top, side and sectional views of the feedthrough device of FIG. 3.

The conductors 24 and pads 24a can be arranged along central horizontal axis X, and also in a series of horizontal rows centered along multiple, a number of, or a plurality of respective horizontal axes $X_x$ that are parallel to or extend in the direction of the X axis. As seen in FIG. 4, there can be 71 conductors 24 that are numbered or labeled as shown from 1-71. The central row of conductors 24 and pads 24a can be centered along the central X axis, and the conductors 24 and pads 24a of adjacent rows can be staggered relative to each other where a conductor 24 and pad 24a of one row can be positioned between two conductors 24 and pads 24a of an adjacent row. The two triangular pads 26a and conductors 26 can be positioned on opposite outer right and left sides or edges of the U-shaped pattern 20 with the apex or triangular points of pads 26a being aligned in the direction of legs 20c and point upwardly in the direction of the Y axis. The bottom or lower side or base of pads 26a can be aligned with the bottom, lower sides or lower arc or curve of the pads 24a that are aligned in the row along central axis X. As a result, the central axis X extends through the bottom portion of pads 26a. This positions the pads 26a generally midway between the top and bottom of the U-shaped pattern 20. The conductor 26 and pad 26a at the right can be labeled RR and at the left can be labeled RL, and can electrically connect to right and left reference lines or reference electrodes. The conductors 24 and pads 24a in alternating rows along axes $X_x$ can also be arranged in a series of vertical columns centered along central vertical axis Y and respective vertical axes $Y_x$, that are parallel to or extend in the direction of the Y axis. The conductors 24 and pads 24a in adjacent vertical columns can be staggered relative to each other, where a conductor 24 and pad 24a of one column can be positioned between two conductors 24 and pads 24a of an adjacent column. Adjacent vertical axes $Y_y$ can be closer together or to each other, than adjacent horizontal axes $X_x$, such as by ½ the distance, making a compact grid. The two pads 26a and conductors 26 on the right and left sides can be aligned with a pad 24a and conductor 24 along respective outer right and left axes $Y_y$. The slot 20b can extend downwardly from the top of the U-shaped pattern 20 and end at the row of conductors 24 and pads 24a centered along central axis X. The slot 20b can have a space vacant of or without conductors 24 and pads 24a extending through and being on the feedthrough member 18, and can have a width equaling in size to about three columns of pads 24a. The slot 20b can be an insulator or insulative slot area of the feedthrough member 18 and U-shaped pattern 20.

The generally U-shaped pattern 20 in some embodiments can include 11 horizontal rows of conductors 24 and 26 along central axis X and axes $X_x$, and 19 vertical columns of conductors 24 and 26 along central axis Y and axes $Y_y$. The axes $X_x$, can include 5 axes above and 5 axes below central axis X, and can be designated as axes +/−($X_1$ through $X_5$), with axes +$X_1$ through +$X_5$ being above central axis X, and axes −$X_1$ through −$X_5$ being below central axis X. The axes $Y_y$, can include 9 axes to the right and 9 axes to the left of central axis Y, and can be designated as +/−($Y_1$ through $Y_9$), with axes +$Y_1$ through +$Y_9$ being to the right of central axis Y, and axes −$Y_1$ through −$Y_9$ being to the left of central axis Y.

Figure 7:
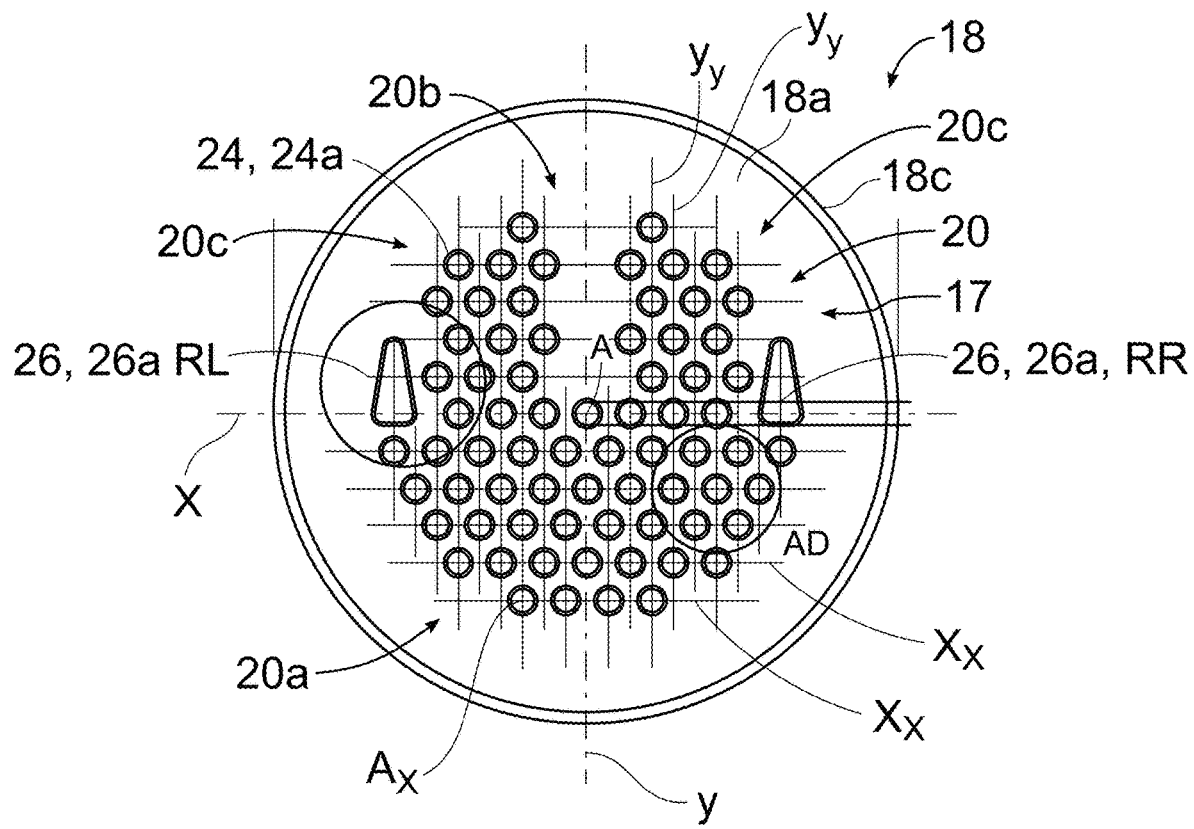
FIGS. 7 and 8 are top and side views on an embodiment of a feedthrough member for a feedthrough device.
Figure 11:
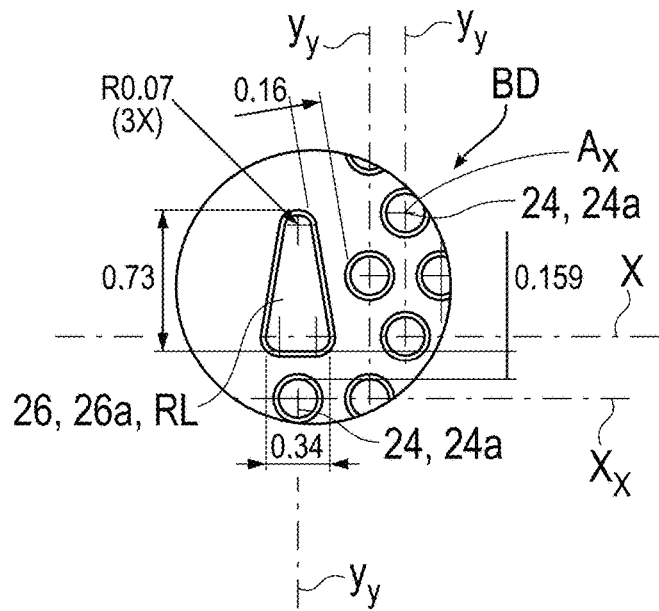
FIGS. 10 and 11 are enlarged top views of portions of a feedthrough member.
Figure 10:
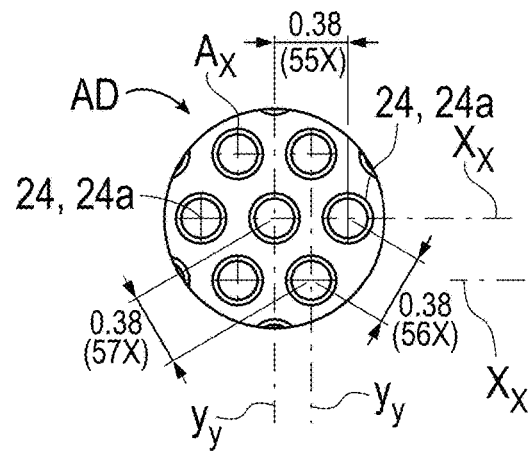
Figure 9:
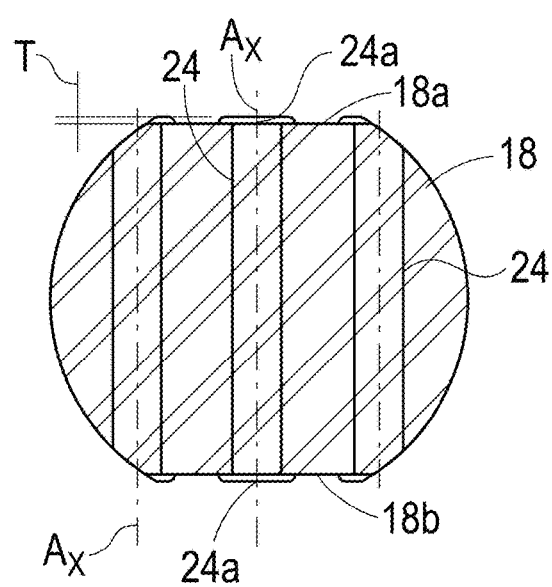
FIG. 9 is an enlarged sectional view of a portion of a feedthrough member.

Referring to FIGS. 7 and 8, embodiments of the feedthrough member 18 can have an outer diameter or width of about 5.5 mm (0.21 inches) and a thickness of about 1.1 mm (0.043 inches). Referring to FIGS. 9-11, the pads 24a associated with conductors 24 can in some embodiments be about 0.026 mm (0.001 inches) in diameter or width, with thickness T of about 0.023 mm (0.0009 inches). Adjacent conductors 24 and pads 24a that are centered along a common row aligned on an axis $X_x$ in the direction of the X axis can be spaced apart about. 38 mm (0.015 inches) center to center, and adjacent conductors 24 and pads 24a that are in two separate rows on respective axes $X_x$ can also be spaced apart about 0.38 mm (0.015 inches) center to center (see detail AD of FIG. 10). As a result, the pads 24a and conductors 24 can be consistently spaced apart from each other in rows and columns along axes X, Y, $X_x$ and $Y_y$. The two triangular pads 26a can have a base that is about 0.34 mm (0.013 inches) wide and can be about 0.73 mm (0.029 inches) high (see detailed BD of FIG. 11), with a thickness T similar to pads 24a. The base of each triangular pad 26a can be spaced about 0.159 mm (0.006 inches) above a round pad 24a, and laterally spaced about 0.16 mm (0.0063) apart from the laterally adjacent round pad 24a.

Figure 13:
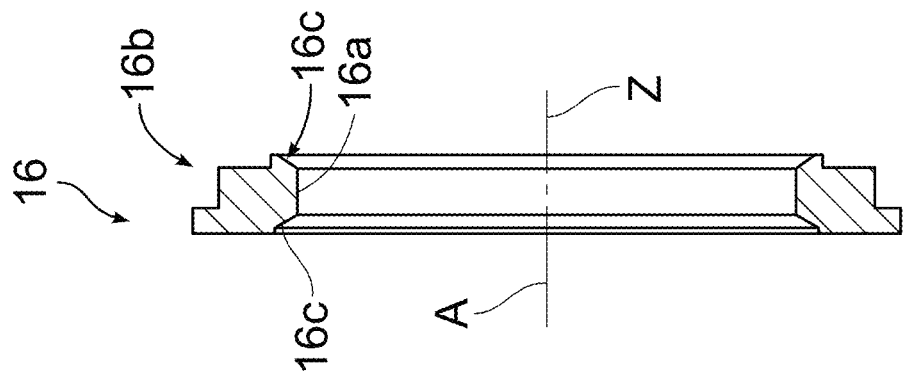
FIGS. 12 and 13 are top and side sectional views of an embodiment of an outer flange for a feedthrough device.
Figure 12:
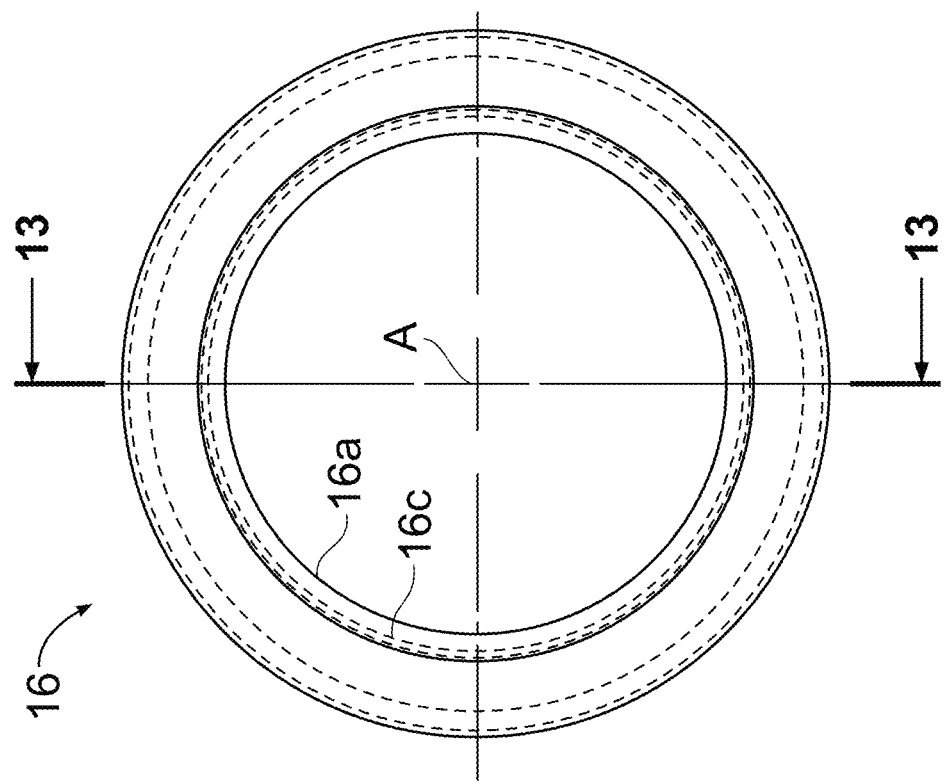

Referring to FIGS. 12 and 13, in some embodiments, outer flange 16 can have a central opening 16a of about 5.6 mm (0.22 inches) and the thickness of about 0.9 mm (0.035 inches).

Referring to FIG. 4, in order to bond wires 22 to the feedthrough device 12, the feedthrough device 12 can be positioned in a bonding apparatus 4 having a bonding head 5 that can move in relation to the feedthrough device 12 for bonding each wire 22 to a designated selected pad 24a or 26a of conductors 24 or 26. An automated recognition device 6 such as machine vision can determine the alignment and orientation of the U-shaped pattern 20 of conductors and either instruct the bonding apparatus 4 to reposition the feedthrough device 12 into a desired orientation, or instruct the bonding head 5 of the orientation to adjust for proper operation. With the U-shaped pattern 20 being centered along central X and Y axes, and the slot 20b being centered along central axis Y, the two triangular pads 26a can be used as visual indicators of the orientation of U-shaped pattern 20, and can be recognized with machine vision. The triangular pads 26a are larger in size than pads 24a, which can allow connection to a larger or bigger diameter wire than pads 24a. In addition, the two legs 20c of the U-shaped pattern 20 can also provide visual indication of orientation. The conductors 24 and 26 and pads 24a and 26a, can be numbered or labeled and can be spaced at known distances from each other relative to the central X and Y axes, so that the bonding head 5 can be instructed or programmed to automatically bond selected wires 22 to selected pads 24a and 26a and conductors 24 and 26 of the U-shaped pattern 20 based on the XY grid. The slot 20b extending to about the center of the U-shaped pattern 20 can allow the bonding head 5 to more easily automatically access centrally located conductors 24 and pads 24a for bonding wires 22 thereto. In some embodiments, normally 64 wires 22 are bonded to the conductors 24 and pads 24a, which can be 71 in number, normally forming 7 unused auxiliary conductors 24 and pads 24a. The auxiliary conductor's 24 and pads 24a can be useful in situations where redundancy is desired, or if situations require more than 64 conductors 24 and pads 24a to be used. The conductors 26 can be right RR and left RL reference lines or leads as labeled on pads 26a, and the conductors 24 labeled 1-71 on the pads 24a can be associated with particular functions or operations of medical implant 10 or connected device 11.

While example embodiments have been particularly shown and described, it will be understood by those skilled in the art that various changes in form and details may be made therein without departing from the scope of the embodiments encompassed by the appended claims.

For example, the use of terms, such as top, bottom, upper, lower, above, below, horizontal, vertical, right, left, etc. are to describe relative positions of features, and it is understood that such terms can change depending upon the orientation of the feedthrough device 12. In addition, although particular dimensions and number of conductors and pads have been shown and described, these can change depending upon the application at hand and in different embodiments. The pads 24a and 26a can also have other suitable shapes and can include more than two shapes. Furthermore, although a generally U-shaped pattern of conductors and pads has been described above, other suitable patterns can be used having an inner, center, or middle portion that is vacant of conductors and pads, for example an annular, O-shaped or ring shaped pattern.

What is claimed is:

1. A feedthrough device comprising:
a feedthrough member formed of insulating material having opposing first and second surfaces; and
a series of conductors extending through the feedthrough member between the first and second surfaces, the series of conductors being arranged in a pattern that has an inner portion vacant of conductors for facilitating access for bonding wires to the conductors on at least one of the first and second surfaces of the feedthrough member.

2. The feedthrough device of claim 1 in which the series of conductors are electrically connected to a respective series of pads that are arranged in a generally U-shaped pattern.

3. The feedthrough device of claim 2 in which the series of conductors are electrically connected to the series of pads on the first and second surfaces of the feedthrough member, a portion of the pads having a first geometric shape, and another portion of the pads having a second geometric shape, for designating at least one of function, alignment and orientation.

4. The feedthrough device of claim 3 in which the pads having the first geometric shape are circular in shape.

5. The feedthrough device of claim 4 in which pads having the second geometric shape are triangular shaped, with triangular points generally aligned in the direction of legs of said generally U-shaped pattern.

6. The feedthrough device of claim 5 in which the generally U-shaped pattern has a generally round periphery and a central slot separating the legs of the generally U-shaped pattern, the triangular shaped pads being positioned at outer edges of the legs of the generally U-shaped pattern.

7. The feedthrough device of claim 6 in which the generally U-shaped pattern is on a hexagonal grid centered on X and Y axes, with the central slot being centered along the Y axis, the pads that are circular in shape being aligned in rows and columns along X and Y axis directions with consistent spacing, and the triangular points of the triangular shaped pads being aligned in the direction of the Y axis, thereby facilitating automated alignment and orientation of the generally U-shaped pattern and automated bonding of said wires to the conductors.

8. The feedthrough device of claim 2 further comprising an outer flange secured to the feedthrough member for supporting the feedthrough member.

9. The feedthrough device of claim 2 in which the series of conductors includes a greater number of conductors than is normally required for most applications, thereby providing additional auxiliary conductors.

10. The feedthrough device of claim 4 in which the pads having the circular shape have a diameter of about 0.26 mm, a center to center spacing of about 0.38 mm, and are 71 in number, whereby 64 pads and associated conductors are normally required for most applications, resulting in additional auxiliary pads and associated conductors.

11. The feedthrough device of claim 5 in which the triangular shaped pads have a base of about 0.34 mm and a height of about 0.73 mm.

12. A feedthrough device comprising:
a feedthrough member formed of insulating material having opposing first and second surfaces; and
a series of conductors extending through the feedthrough member between the first and second surfaces, the series of conductors being arranged in a generally U-shaped pattern having a generally round periphery and a central slot for facilitating access for bonding wires to the conductors on at least one of the first and second surfaces of the feedthrough member, the series of conductors being electrically connected to pads on the first and second surfaces of the feedthrough member, a portion of the pads having a circular shape, and two of the pads on opposite sides of the generally U-shaped pattern having a triangular shape, for designating at least one of function, alignment and orientation.

13. A method of electrically connecting wires to a feedthrough device comprising:
providing a feedthrough member formed of insulating material having opposing first and second surfaces, a series of conductors extending through the feedthrough member between the first and second surfaces, the series of conductors being arranged in a pattern that has an inner portion vacant of conductors; and
bonding the wires to the conductors on at least one of the first and second surfaces of the feedthrough member, the pattern having the inner portion vacant of conductors facilitating access for bonding the wires to the conductors.

14. The method of claim 13 in which the series of conductors are electrically connected to a respective series of pads that are arranged in a generally U-shaped pattern.

15. The method of claim 14 in which the series of conductors are electrically connected to the series of pads on the first and second surfaces of the feedthrough member, a portion of the pads having a first geometric shape, and another portion of the pads having a second geometric shape, the method further comprising designating at least one of function, alignment and orientation with the first geometric shape and the second geometric shape.

16. The method of claim 15 in which the pads having the first geometric shape are circular in shape.

17. The method of claim 16 in which pads having the second geometric shape are triangular shaped, with triangular points generally aligned in the direction of legs of said generally U-shaped pattern.

18. The method of claim 17 in which the generally U-shaped pattern has a generally round periphery and a central slot separating the legs of the generally U-shaped pattern, the triangular shaped pads being positioned at outer edges of the legs of the generally U-shaped pattern.

19. The method of claim 18 in which the generally U-shaped pattern is on a hexagonal grid centered on X and Y axes, with the central slot being centered along the Y axis, the pads that are circular in shape being aligned in rows and columns along X and Y axis directions with consistent spacing, and the triangular points of the triangular shaped pads being aligned in the direction of the Y axis, the method further comprising automating alignment and orientation of the generally U-shaped pattern and automating bonding of the wires to the conductors.

20. The method of claim 14 in which an outer flange is secured to the feedthrough member for supporting the feedthrough member.

21. The method of claim 14 further comprising providing additional auxiliary conductors by including a greater number of conductors in the series of conductors than is normally required for most applications.

22. The method of claim 16 in which the pads having the circular shape have a diameter of about 0.26 mm. a center to center spacing of about 0.38 mm, and are 71 in number, whereby 64 pads and associated conductors are normally required for most applications, resulting in additional auxiliary pads and associated conductors.

23. The method of claim 17 in which the triangular shaped pads have a base of about 0.34 mm and a height of about 0.73 mm.

* * * * *